US005123916A

United States Patent [19]

Riddle et al.

[11] Patent Number: 5,123,916

[45] Date of Patent: Jun. 23, 1992

[54] LUMBAR SPINE THERAPY DEVICE

[75] Inventors: George E. Riddle, Anderson County; Ronnie J. Withrow, McMinn County; George M. Cox, Campbell County; James L. Aslinger, Anderson, County all of Tenn.

[73] Assignee: United Apothecary, Inc., Oak Ridge, Tenn.

[21] Appl. No.: 640,945

[22] Filed: Jan. 14, 1991

[51] Int. Cl.[5] .......... A61F 5/00

[52] U.S. Cl. .......... 606/243; 606/242

[58] Field of Search .......... 128/70-75; 269/322-325

[56] References Cited

U.S. PATENT DOCUMENTS

| | | | |
|---|---|---|---|
| 1,190,195 | 7/1916 | Schmidt | 128/74 |
| 1,830,071 | 11/1931 | Patton | 128/72 |
| 2,002,349 | 5/1935 | Lundeen | 128/72 |
| 2,104,745 | 1/1938 | Howell et al. | 128/74 X |
| 2,152,431 | 3/1939 | Jensen | 128/74 |
| 2,179,595 | 11/1939 | McManis | 128/72 |
| 2,865,367 | 12/1958 | Sorenson | 128/71 |
| 2,931,354 | 4/1960 | Sellner | 128/74 X |
| 3,241,828 | 3/1966 | Adolphson et al. | 128/72 X |
| 3,674,017 | 7/1972 | Stefani, Jr. | 128/25 R |
| 4,144,880 | 3/1979 | Daniels | 128/74 X |
| 4,649,905 | 3/1987 | Barnes | 128/74 |
| 4,655,200 | 4/1987 | Knight | 128/71 |

*Primary Examiner*—Richard J. Apley
*Assistant Examiner*—Linda C. M. Dvorak
*Attorney, Agent, or Firm*—Pitts and Brittian

[57] ABSTRACT

A lumbar spine therapy device (10) for passively exercising the muscle groups especially surrounding the lumbar spine for postoperative and other rehabilitative therapy such as to allow normal collagen formation to occur, thus minimizing scarring and quickening a return to normal function and development of strength in both the muscles of function as well as the secondary support system. The lumbar spine therapy device (10) includes a frame (12) for engaging a support surface (32). A body support (14) is provided for supporting the body a patient and includes a stationary support (64) for supporting the buttocks region of a patient and pivoting supports (78) for supporting the torso and legs of a patient. A motor (92) is provided for driving at least one pivoting support oscillator (18), the oscillators (18) being provided to oscillate each pivoting support (78) independently. An amplitude adjuster (20) is connected to each oscillator (18) for altering the amplitude of displacement. A control box (22) is provided for carrying the motor controls, including at least a patient control button (24) and an emergency stop button (26). A restraining belt (28) is provided to prevent a patient from slipping along the body support (14). Casters (170) with locking wheels (172) are provided to aid in easy transporting of the device (10).

10 Claims, 3 Drawing Sheets

LUMBAR SPINE THERAPY DEVICE

DESCRIPTION

1. Technical Field

This invention relates to the field of postoperative spinal therapy. Specifically, this invention relates to an apparatus used in the postoperative rehabilitation of the lumbar spine to regain strength and function.

2. Background Art

In the field of postoperative spinal therapy, it is well known that serious loss of motion, painful contractures and stiffness may occur, particularly in the lumbar spine. It is also well known that rehabilitation is difficult in that the normal collagen formation cannot occur and disorganized scar results which further impedes the healing process and recovery.

Other devices have been produced to exercise the human body for rehabilitative or other purposes. Typical of the art are those devices disclosed in U.S. Pat. Nos. 2,152,431 issued to S. H. Jensen on Mar. 28, 1939; 2,598,204 issued to R. E. Allen on May 27, 1952; and 3,315,666 issued to J. W. Sellnor on Apr. 25, 1967; 3,450,132 issued to C. A. Ragon, et al. on Jun. 17, 1969; 3,623,480 issued to R. F. Chisholm on Nov. 30, 1971; 3,674,017 issued to H. Stefani, Jr. on Jul. 4, 1972; 4,531,730 issued to R. Chenera on Jul. 30, 1985; 4,827,913 issued to A. E. Parker on May 9, 1989; and 4,834,072 issued to L. M. Goodman on May 30, 1989. Each of these devices are designed to exercise the human body in some fashion for strengthening, stretching, relaxing, reducing weight, or some other related function. None of these, however, is designed specifically for exercising a patient's spine as a rehabilitation technique following surgery, or for patients suffering from chronic deconditioned spines. For example, the 3,623,480 ('480), 3,674,017 ('017), and 4,827,913 ('913) patents are most useful in exercising the abdomen region. However, these designs employ a single pivoting support surface, the surface being pivoted in a range from substantially the horizontal plane upward to substantially the vertical plane. The 4,834,072 ('072) patent discloses an invention which is specifically designed to exercise the legs in like manner by elevating the legs simultaneously or individually above or below the horizontal plane, with no other body parts being exercised. The 3,450,132 ('132) patent is designed to exercise the feet, legs, hips, back, arms, shoulders and neck of a patient suffering from polio or other form of paralysis or muscular disorder.

The desired exercise for postoperative spinal therapy begins with the patient lying in a substantially horizontal plane, the torso and head then being lowered to an angle below the horizontal as the legs are also lowered at the same rate and amplitude, the buttocks remaining stationary throughout. The torso and legs are then raised to the starting position and the processed repeated a desired number of times or for a desired duration. The 2,152,431 ('431), 2,598,204 ('204), 3,315,666 ('666), and 4,531,730 ('730) patents disclose devices which may be used to acquire this type of motion, however, they are not designed specifically for the postoperative treatment of spinal patients and offer a much larger range of motion than is desired, along with other features unnecessary or inappropriate for such treatment. For example, the '666 patent is designed to massage a user's back or other body part, depending on how the device is employed, and requires the motion of the user to manipulate the device as opposed to an external power source. This, of course, is undesirable due to the weakened condition of the spinal patient. The '666 patent does not provide for a stationary buttocks support, thereby preventing the isolation of the desired muscles for rehabilitation. Likewise, the '730 patent is ineffective because it is designed specifically for stretching the legs of a user in order to improve leg flexibility. The '730 patent is also manually operated with no means for limiting the range of motion of each repetition.

Therefore, it is an object of this invention to provide a means for passively exercising the muscle groups especially surrounding the lumbar spine for postoperative and other rehabilitative therapy.

Another object of this invention is to provide a means whereby the normal collagen formation may occur, thus minimizing scarring and allowing a faster return to normal function and development of strength in both the muscles of function as well as the secondary support system.

It is also an object of this invention to provide a means whereby the upper body and lower body are simultaneously exercised.

Another object of this invention is to provide a means whereby the range of motion is independently selected for the upper and lower body.

Still another object of this invention is to provide a drive means to power both the upper body and lower body exercise means.

Yet another object of this invention is to provide a means whereby the patient may control the operation of the device.

DISCLOSURE OF THE INVENTION

Other objects and advantages will be accomplished by the present invention which serves to passively exercise the muscle groups especially surrounding the lumbar spine for postoperative and other rehabilitative therapy. The lumbar spine therapy device includes a frame means for engaging a support surface. The frame means is fabricated from a lightweight, rigid material such as tubular steel or the like. In the preferred embodiment, the frame means has a substantially box-shaped configuration with a length and width to support a selected size body support means. The height of the frame means is dimensioned such that a patient may easily position his/her body on the body support means, or in the case of an inambulant patient, medical attendants may easily move the patient from a typical bed to the device.

The body support means is provided for supporting the body of a patient. The body support means includes a stationary support means and a first and second pivoting support means. The stationary support means is provided to support the buttocks region of the patient. The stationary support means is connected to the frame means proximate the middle portion such that the stationary support means is elevated above the frame means. The stationary support means of the preferred embodiment has a substantially rectangular configuration and is dimensioned to comfortably seat a patient of a selected size. In the preferred embodiment, the stationary support includes a planar member with a cushion attached to the top side for the comfort of the patient, especially when extended use is required. The first pivoting support means is provided for supporting at least the torso of a patient. The second pivoting support means is provided for supporting at least the upper legs of a patient. The first and second pivoting support means of the preferred embodiment are substantially similar and have a substantially planar, rectangular configuration. The pivoting supports of this embodiment are hingeably connected about one end to opposing sides of the stationary support means with a plurality of hinges. The first and second pivoting support displacement means are connected to the first and second pivoting supports, respectively, proximate the bottom side. The pivoting supports of the preferred embodiment are fabricated from a rigid material such as wood or sheet metal. A cushion may be provided to cover the pivoting supports for the comfort of the patient.

A drive means is provided for simultaneously oscillating the first and second pivoting support means. The drive means is powered by a selected motor commonly used in the art, the speed of the motor being variably controlled. A transmission is connected between the motor for controlling the rotational velocity of a drive shaft in relation to the rotational velocity of the motor. The drive shaft is connected to at least one pivoting support displacement means. The drive means of the preferred embodiment is connected to at least one lateral support member of the frame means.

The pivoting support displacement means is provided for oscillating the first and second pivoting supports. In the preferred embodiment, a first and second pivoting support displacement means are provided for respectively oscillating the first and second pivoting supports independently. The pivoting support displacement means includes a chain-driven gear. An axle extends from the center of the gear and engages a cam, a push rod being connected eccentrically to the cam. The push rod is also connected to the pivoting support such that as the cam is rotated, the bottom end of the push rod is moved in a circular direction, causing the top end of the push rod to move in a substantially vertical direction, thus displacing the pivoting support to which the push rod is attached.

A displacement adjustment means is connected to the pivoting support displacement means for selectively altering the amplitude of displacement. In the preferred embodiment, a plurality of openings are defined by the cam and are spaced apart radially away from the axle. The openings are configured to receive the selected bolt used to attach the push rod. The opening farthest from the axle has the greatest eccentricity and therefore will yield the greatest displacement of the pivoting support. Likewise, the opening closest the axle is the least eccentric and will therefore yield the least displacement.

A control box is provided for the location of the motor controls. The control box includes at least an on/off switch for the selective operation of the motor and a speed regulator for adjusting the speed of the motor. A patient control means is provided such that a patient may remotely control the speed of the drive means while using the device. The patient control means of the preferred embodiment is configured to be easily held by the user such that the desired exercise may be performed without requiring the patient to alter his position during exercise. The control button is designed to function at least as a remote on/off switch and conceivably as a speed control or other desired function. In the preferred embodiment, the patient control means is connected proximate the control box with a plug-in type jack or other conventional method. An emergency stopping means is provided to interrupt operation of the device when required. In the preferred embodiment, the emergency stopping means includes an on/off switch designed to override all other controls in order to arrest the movement of the pivoting supports.

A restraining means is provided to prevent a patient from slipping along the surface of the body support means when the device is in operation. In the preferred embodiment, the restraining means includes at least a belt designed to be secured around the waist of the patient.

A mobilization means is provided such that the device may be easily transported. In the preferred embodiment, the mobilization means includes a plurality of casters provided with wheel locks, commonly known in the art. Casters are attached to the frame means at least proximate each corner of the bottom of the frame means.

BRIEF DESCRIPTION OF THE DRAWINGS

The above mentioned features of the invention will become more clearly understood from the following detailed description of the invention read together with the drawings in which.

BEST MODE FOR CARRYING OUT THE INVENTION

Figure 1:
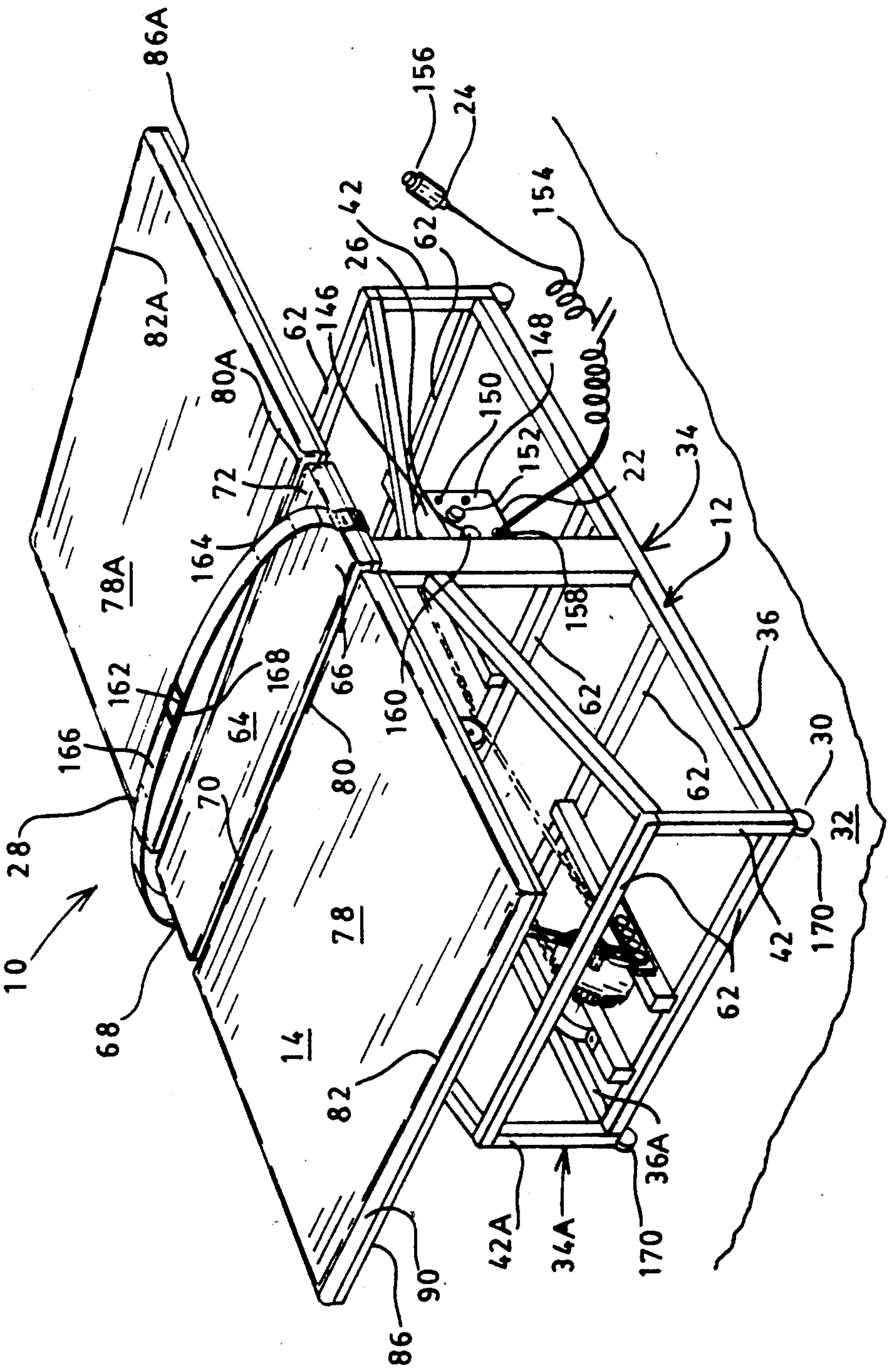
FIG. 1 is a perspective view of the lumbar spine therapy device constructed in accordance with several features of the present invention.
Figure 2:
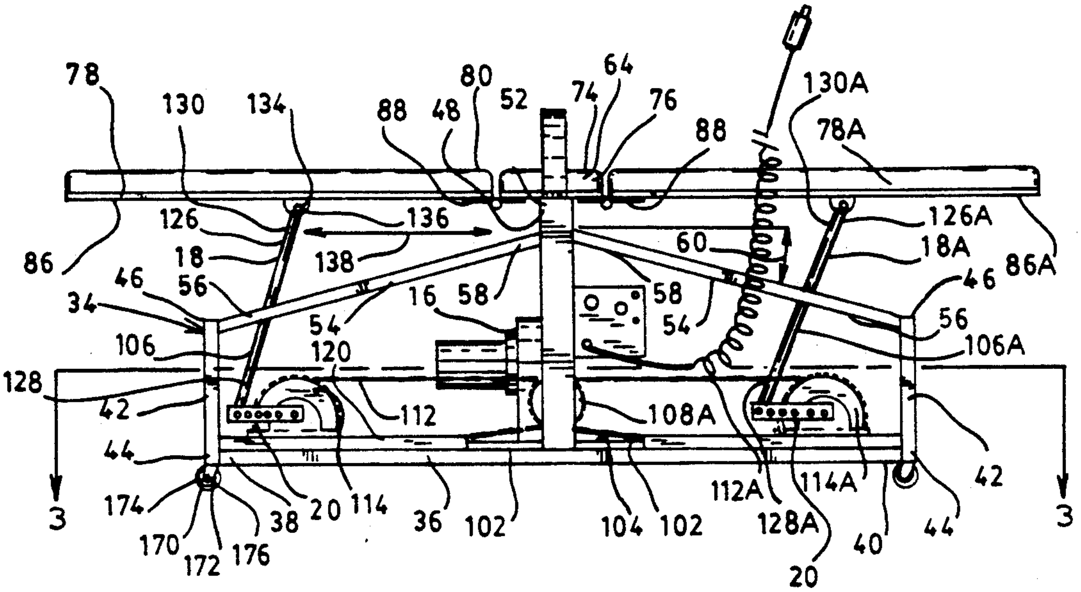
FIG. 2 illustrates a front elevation view of the lumbar spine therapy device shown in FIG. 1.
Figure 3:
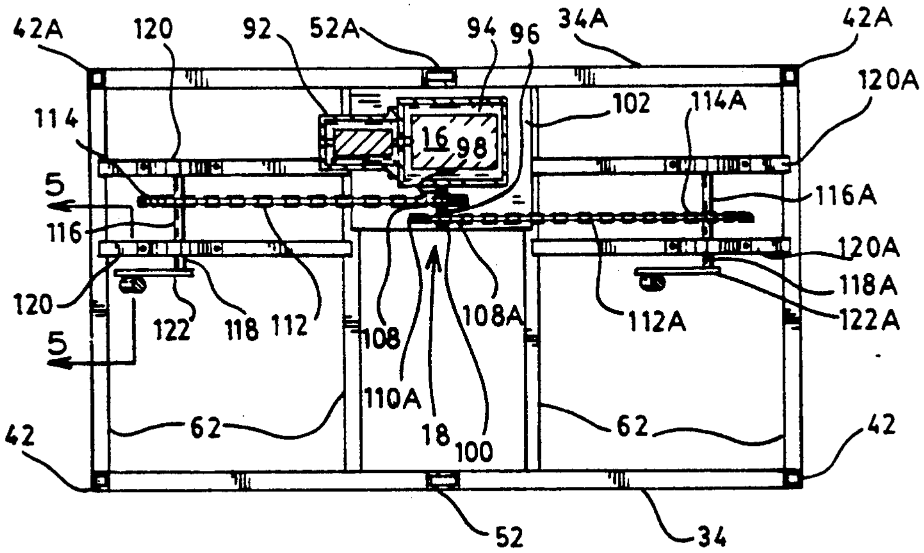
FIG. 3 is a top elevation view, in section, of the lumbar spine therapy device taken at 3—3 of FIG. 2.
Figure 4:
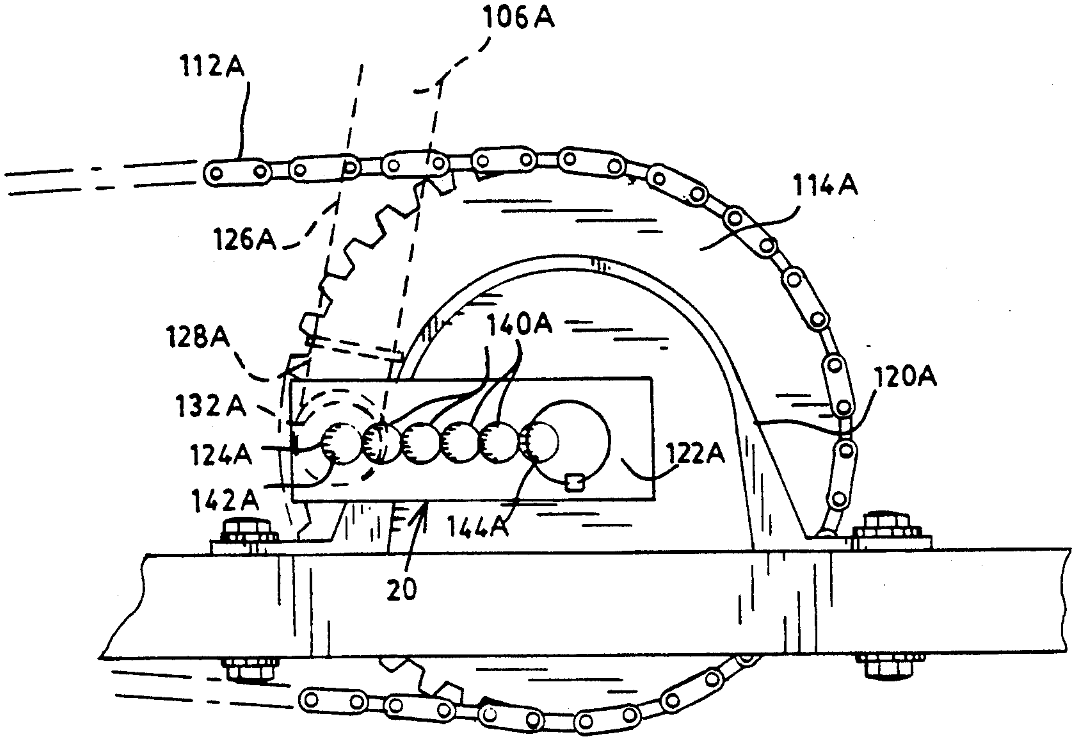
FIG. 4 illustrates a partial front elevation view of the lumbar spine therapy device showing the amplitude adjustment means, the push rod of the pivoting support displacement means being shown in phantom.

A lumbar spine therapy device incorporating various features of the present invention is illustrated generally at 10 in the figures. The lumbar spine therapy device 10 is designed for passively exercising the muscle groups especially surrounding the lumbar spine for postoperative and other rehabilitative therapy such as to allow normal collagen formation to occur, thus minimizing scarring and allowing a faster return to normal function and development of strength in both the muscles of function as well as the secondary support system.

The lumbar spine therapy device 10 includes a frame means 12 for engaging a support surface 32. The frame means 12 is fabricated from a lightweight, rigid material such as tubular steel or the like. In the preferred embodiment, the frame means 12 has a substantially box-shaped configuration with a length and width to support a selected size body support means 14. The height of the frame means 12 is dimensioned such that a patient may easily position his/her body on the body support means 14, or in the case of an inambulant patient, medical attendants may easily move the patient from a typical bed to the device 10. The frame means 12 of the preferred embodiment includes a pair of laterally disposed faces 34 connected by a plurality cf lateral braces 62. The face 34 of this embodiment has a substantially rectangular configuration including a substantially horizontal member 36. First and second upwardly extending vertical members 42 are attached to the horizontal member first and second ends 38, 40 at substantial right angles. A third upwardly extending vertical member 48 is connected to the horizontal member 36 proximate the middle at a substantial right angle. The first ends 56 of first and second top members 54 are respectively connected to the second ends 46 of the first and second vertical members 42. The second ends 58 of the first and second top members 54 are connected along the third vertical member 48 proximate the second end 52 at an elevation above the top member first ends 56, the second end 52 of the third vertical member 48 extending above the first and second top member first ends 56. Thus from the top member second end 58 to the top member first ends 56, a vertical angle 60 below the horizontal is defined. The angle 60 is substantially equal to the range of motion of the body support means 14 of the lumbar spine therapy device 10 below the horizontal, as is discussed below. In the preferred embodiment, the angle 60 is substantially fifteen (15) degrees, but may be varied as required. In the preferred embodiment, lateral braces 62 are provided to adjoin the first and second faces 34, 34A as shown or as otherwise desired. Face 34A is substantially similar to face 34 as described and is thus labelled with like numerals followed by "A". The various connections described may be of a method commonly understood such as welding or bolting, but may also include methods not yet known.

The body support means 14 is provided for supporting the body a patient. The body support means 14 includes a stationary support means 64 and a first and second pivoting support means 78, 78A. The stationary support means 64 is provided to support the buttocks region of the patient and to act as a reference point for the displacement of the first and second pivoting support means 78, 78A. The stationary support means 64 is connected to the seconds ends 52 of the third vertical members 48 of the frame means 12 such that the stationary support means 64 is elevated above the frame means 12. The stationary support means 64 of the preferred embodiment has a substantially rectangular configuration and is dimensioned to comfortably seat a patient of a selected size. In the preferred embodiment, the stationary support means 64 is substantially planar and is fabricated from a rigid material such as wood, sheet metal, or the like. A cushion 76 may be provided to attach to the top side 74 for the comfort of the patient, especially when extended use is required.

The first pivoting support means 78 is provided for supporting at least the torso of a patient. The first pivoting support means 78 of the preferred embodiment is substantially planar and has a substantially rectangular configuration. The first pivoting support means 78 of this embodiment is hingeably connected about the first end 80 to the first side 70 of the stationary support means 64 with a plurality of hinges 88. The first pivoting support displacement means 106 is connected to the first pivoting support means 78 proximate the bottom side 86, as discussed below. The first pivoting support displacement means 106 thus acts to control the elevation of the second end 82 of the first pivoting support means 78. The first pivoting support means 78 of the preferred embodiment is fabricated from a rigid material such as wood or sheet metal. A cushion 90 may be provided to cover the first pivoting support means 78 for the comfort of the patient.

The second pivoting support means 78A is provided for supporting at least the upper legs of a patient. The second pivoting means 78A is substantially similar to the first pivoting support means 78 and is thus labeled with like numerals followed by "A". The first end 80A of the second support means 78A is hingeably connected to the stationary support means 64 proximate the second side 72. The second pivoting support means 78A is connected proximate its bottom side 86A to the second pivoting support displacement means 106A in similar fashion as the first pivoting support means 78. The first and second pivoting support means 78, 78A are configured such that as the first and second pivoting support displacement means 106, 106A are operated, the first and second pivoting support means 78, 78A oscillate simultaneously such that the feet and head of the patient are displaced the greatest distance.

A drive means 16 is provided for simultaneously oscillating the first and second pivoting support means 78, 78A. The drive means 16 is powered by a selected motor 92 commonly used in the art. In the preferred embodiment, the rotational velocity of the motor 92 may be variably controlled. The first end 98 of a drive shaft 96 is connected to the motor 92, the second end 100 of the drive shaft 96 being connected to at least one pivoting support displacement means 18. In the preferred embodiment, a transmission 94 is connected between the motor 92 and the drive shaft 96 for controlling the rotational velocity of the drive shaft 96 in relation to the rotational velocity of the motor 92. The drive means 16 of the preferred embodiment is connected to the top 104 of a plate 102 with conventional means such as welding or bolting, the plate 102 being attached to at least one lateral brace 62.

Figure 5:
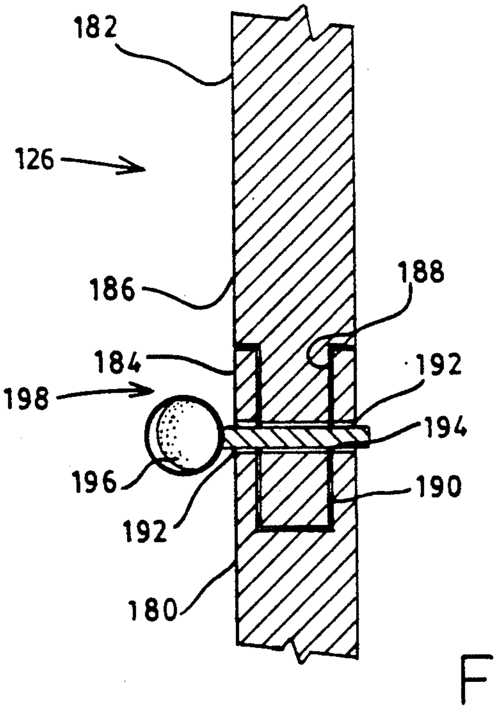
FIG. 5 is a partial front elevation view, in section, of an alternate embodiment of the push rod taken at 5—5 of FIG. 3.

A pivoting support displacement means 18 is provided for oscillating the first and second pivoting support means 78–78A. In the preferred embodiment, first and second pivoting support displacement means 106–106A are provided for respectively oscillating the first and second pivoting support means 78–78A independently. The first and second pivoting support displacement means 106–106A are substantially similar and will therefore be referred to as "the pivoting support displacement means 106" hereafter unless otherwise required, like parts being referred to with like numerals with the designation "A" following the numbers in the drawings and description of the second pivoting support displacement means 106A. The pivoting support displacement means 106 includes a pinion 108 which is attached to the drive shaft 96 of the drive means 16 proximate the second end 100. The pinion 108 includes a sprocket 110 configured to engage a chain 112. A gear 114 is in turn driven by the chain 112. An axle 116 extends from the center of the gear 114 and is journaled to a plurality of support blocks 120, each support block 120 being attached to the frame means 12 by a conventional method. In the preferred embodiment, the axle 116 is journaled to at least two support blocks 120, at least one support block 120 being located on either side of the gear 114 to secure the axle 116 from undesired movement. A displacement Cam 122 is affixed to the first end 118 of the axle 116, the cam 122 thus rotating as the gear 114 is rotated. The first end 128 of a push rod 126 is journaled to the cam 122 eccentrically such that as the cam 122 is rotated, the first end 128 of the push rod 126 is moved in a circular direction. In the preferred embodiment, the cam 122 defines a threaded opening 124 dimensioned to receive a selected bolt 132. The first end 128 of the push rod 126 has a substantial "eye" configuration dimensioned to loosely receive the selected bolt 132 inserted into the cam 122. The second end 130 of the push rod 126 is journally connected to the bottom side 86 of the pivoting support means 78 a distance 138 from the first end 80 so that as the first end 128 of the push rod 126 is moved in a circular motion, the second end 130 of the push rod 126 and the pivoting support means 78 are displaced vertically. The second end 130 of the push rod 126 of the preferred embodiment has a substantial "eye" configuration and is dimensioned to be received by a clevis 134 and held in place with a selected pin 136, bolt or the like. In the embodiment shown in FIG. 5, the push rod 126 includes a first leg 180 and a second leg 182, the first and second legs 180, 182 being connected about the second and first ends 184, 186, respectively. The first leg second end 184 defines a recess 188 dimensioned to receive an extended portion 190 extending axially from the second leg first end 186 such as to define the connection 198. The connection 198 is provided as a safety feature such that an observer may selectively disengage a pivoting support means 78 simply by holding the pivoting support means second end 82 and lifting upward, thus disengaging the second leg 182 from the first leg 180. A through hole 192 may be defined proximate the first leg second end 184 to cooperate with a through hole 194 defined by the second leg extended portion 190 in order to receive a pin 196 to selectively secure the first and second legs 180, 182 during transport or as otherwise required.

A displacement adjustment means 20 is connected to the pivoting support displacement means 18 for selectively altering the amplitude of displacement. In the preferred embodiment, a plurality of openings 140 are defined by the cam 122 and are spaced apart radially away from the axle 116. The openings 140 are threaded to receive the selected bolt 132 used to attach the push rod 126 as described above. The opening 142 spaced farthest from the axle 116 has the greatest eccentricity and therefore will yield the greatest displacement of the pivoting support means 78. Likewise, the opening 144 spaced closest to the axle 116 is the least eccentric and will therefore yield the least displacement. It is envisioned that the displacement adjustment means 20 may alternatively be connected to the pivoting support means 78 proximate the push rod second end 130 if required, the amplitude adjustment being a resultant of varying the distance 138 between the push rod second end 130 and the pivoting support means first end 80.

A control box 22 is provided for the location of the motor controls. The control box 22 includes at least an on/off switch 150 for the selective operation of the motor 92 and a speed regulator 152 for adjusting the speed of the motor 92. In the preferred embodiment, the control box 22 is connected to the frame means 12 proximate the first side panel 34 in a conventional manner such as by bolting or welding. The control box 22 of the preferred embodiment includes a junction box 146 and a cover plate 148. The junction box 146 and cover plate 148 are fabricated from a rigid or semi-rigid material such as metal or plastic. In the preferred embodiment, the junction box 146 is of a type readily available in the market.

A patient control means 24 is provided such that a patient may remotely control the speed of the drive means 16 while using the device 10. The patient control means 24 includes an extension cord 154 with a control button 156 at one end. The control button 156 of the preferred embodiment is configured to be easily held by the user such that the desired exercise may be performed without requiring the patient to alter his position during exercise. The control button 156 is designed to function at least as a remote on/off switch 150 and conceivably as a speed control 152 or other desired function. In the preferred embodiment, the patient control means 24 is connected proximate the control box 22 with a plug-in type jack 158 or other conventional method.

An emergency stopping means 26 is provided to interrupt operation of the device 10 when required. In the preferred embodiment, the emergency stopping means 26 is carried by the control box 22 and includes an on/off switch 160 designed to override all other controls in order to arrest the movement of the pivoting support means 78. The emergency stopping means 26 may be used when the patient feels an excess of discomfort or when a malfunction occurs or the patient is otherwise unable to stop the device 10.

A restraining means 28 is provided to prevent a patient from slipping along the body support means 14 when the device 10 is in operation. In the preferred embodiment, the restraining means 28 includes at least a belt 162 designed to be secured around the waist of the patient. The embodiment shown in the figures includes a first strap 164 connected to the first end 66 of the stationary support means 64 and a second strap 166 connected to the second end 68 of the stationary support means 64. In the preferred embodiment, the first strap 164 is releasably secured to the second strap 166 by a conventional method such as a hook-and-loop type fastener 168. The restraining means 28 is fabricated from a pliable material such as nylon or leather.

A mobilization means 30 is provided such that the device 10 may be easily transported. In the preferred embodiment, the mobilization means 30 includes a plurality of casters 170, commonly known in the art. In this embodiment, the casters 170 are connected to the frame means 12 such as to engage a support surface 32. Casters 170 are attached to the frame means 12 at least proximate the first ends 44 of the frame means first and second vertical members 42. The mobilization means 30 of the preferred embodiment includes braking means 172 to prevent the device 10 from unselected movement. The casters 170 of the preferred embodiment include wheel locks 172 which may be engaged by pressing one end 174 and disengaged by pressing the opposing end 176.

From the foregoing description, it will be recognized by those skilled in the art that a lumbar spine therapy device offering advantages over the prior art has been provided. Specifically, the lumbar spine therapy device provides a means for passively exercising the muscle groups especially surrounding the lumbar spine for postoperative and other rehabilitative therapy such as to allow normal collagen formation to occur, thus minimizing scarring and allowing a faster return to normal function and development of strength in both the muscles of function as well as the secondary support system.

While a preferred embodiment has been shown and described, it will be understood that it is not intended to limit the disclosure, but rather it is intended to cover all modifications and alternate methods falling within the spirit and the scope of the invention as defined in the appended claims.

Having thus described the aforementioned invention, I claim:

1. A lumbar spine therapy device for passively exercising the muscle groups especially surrounding the lumbar spine for postoperative and other rehabilitative therapy such as to allow normal collagen formation to occur, thus minimizing scarring and allowing a faster return to normal function and development of strength in both the muscles of function as well as the secondary support system, said lumbar spine therapy device comprising:

a frame means for structurally supporting said lumbar spine therapy device and any loads applied thereto;

a stationary support means secured to said frame means for supporting the buttocks of a user;

a first pivoting support member for supporting at least the torso of a user, said support member being hingeably attached about one end to said frame means proximate one side of said stationary support means;

a second pivoting support member for supporting at least the upper legs of a user, said support member being hingeably attached about one end to said frame means proximate the side of said stationary support means opposite said first pivoting support member; and a drive means for simultaneously oscillating said first and second pivoting support members about said hinged ends a selected angle from the horizontal plane, said drive means including a selected motor with a drive shaft connected to at least one pivoting support displacement means, said pivoting support displacement means including a pinion connected to said drive shaft, a chain pulled by said pinion, a gear driven by said chain, a push rod journally connected at one end to said gear and journally connected at a second end to said pivoting support member, and a displacement adjusting means connected to said push rod for selectively adjusting the amplitude of displacement.

2. The lumbar spine therapy device of claim 1 wherein said displacement adjusting means includes an attachment rod connected to said gear and extending radially therefrom, said attachment rod defining a plurality of openings for attaching said end of said push rod, said openings being spaced linearly away from an axis perpendicular to the center of said gear and dimensioned to be journally connected to said end of said push rod such that as said gear is rotated, said end of said push rod is displaced eccentrically thereby causing said pivoting support to oscillate in the substantially vertical direction.

3. The lumbar spine therapy device of claim 1 wherein said displacement from said horizontal plane is substantially equal above said horizontal and below said horizontal.

4. The lumbar spine therapy device of claim 1 wherein said selected displacement angle of said first pivoting support member is selected independently from said selected displacement angle of said second pivoting support member.

5. A lumbar spine therapy device for passively exercising the muscle groups especially surrounding the lumbar spine for postoperative and other rehabilitative therapy such as to allow normal collagen formation to occur, thus minimizing scarring and allowing a faster return to normal function and development of strength in both the muscles of function as well as the secondary support system, said lumbar spine therapy device comprising:

a frame means for structurally supporting said lumbar spine therapy device and any loads applied thereto;

a stationary support means secured to said frame means for supporting the buttocks of a user;

a first pivoting support member for supporting at least the torso of a user, said support member being hingeably attached about one end to said frame means proximate one side of said stationary support means;

a second pivoting support member for supporting at least the upper legs of a user, said support member being hingeably attached about one end to said frame means proximate the side of said stationary support means opposite said first pivoting support member;

a drive means for simultaneously oscillating said first and second pivoting support members about said hinged ends a selected angle from the horizontal plane, said drive means including a selected motor with a drive shaft connected to at least one pivoting support displacement means;

said pivoting support displacement means including a pinion connected to said drive shaft, a chain pulled by said pinion, a gear driven by said chain, a push rod journally connected at one end to said gear and journally connected at a second end to said pivoting support, and a displacement adjusting means connected to said push rod for selectively adjusting the amplitude of displacement, said amplitude of displacement from said horizontal plane being substantially equal above said horizontal and below said horizontal; and said displacement adjusting means including an attachment rod connected to said gear and extending radially therefrom, said attachment rod defining a plurality of openings for attaching said end of said push rod, said openings being spaced linearly away from an axis perpendicular to the center of said gear and dimensioned to be journally connected to said end of said push rod such that as said gear is rotated, said push end of said push rod is displaced eccentrically thereby causing said pivoting support to oscillate in the substantially vertical direction, said selected displacement angle of said first pivoting support member being selected independently from said selected displacement angle of said second pivoting support member.

6. The lumbar spine therapy device of claim 5 which further comprises a patient control means for allowing a patient to remotely and selectively vary the speed of said drive means.

7. The lumbar spine therapy device of claim 5 which further comprises an emergency stopping means for stopping said drives means as required.

8. A lumbar spine therapy device for passively exercising the muscle groups especially surrounding the lumbar spine for postoperative and other rehabilitative therapy such as to allow normal collagen formation to occur, thus minimizing scarring and allowing a faster return to normal function and development of strength in both the muscles of function as well as the secondary support system, said lumbar spine therapy device comprising:

a frame means for structurally supporting said lumbar spine therapy device and any loads applied thereto;

a stationary support means secured to said frame means for supporting the buttocks of a user;

a first pivoting support member for supporting at least the torso of a user, said support member being hingeably attached about one end to said frame means proximate one side of said stationary support means;

a second pivoting support member for supporting at least the upper legs of a user, said support member being hingeably attached about one end to said frame means proximate the side of said stationary support means opposite said first pivoting support member;

a drive means for simultaneously oscillating said first and second pivoting support members about said hinged ends a selected angle from the horizontal plane, said drive means including a selected motor with a drive shaft connected to at least one pivoting support displacement means;

said pivoting support displacement means including a pinion connected to said drive shaft, a chain pulled by said pinion, a gear driven by said chain, a push rod journally connected at one end to said gear and journally connected at a second end to said pivoting support, and a displacement adjusting means connected to said push rod for selectively adjusting the amplitude of displacement, said amplitude of displacement from said horizontal plane being substantially equal above said horizontal and below said horizontal; and said displacement adjusting means including an attachment rod connected to said gear and extending radially therefrom, said attachment rod defining a plurality of openings for attaching said end of said push rod, said openings being spaced linearly away from an axis perpendicular to the center of said gear and dimensioned to be journally connected to said end of said push rod such that as said gear is rotated, said push end of said push rod is displaced eccentrically thereby causing said pivoting support to oscillate in the substantially vertical direction, said selected displacement angle of said first pivoting support member being selected independently from said selected displacement angle of said second pivoting support member;

a patient control means for allowing a patient to remotely and selectively vary the speed of said drive means; and an emergency stopping means for stopping said drives means as required.

9. The lumbar spine therapy device of claim 8 which further comprises a restraining means for securing said patient from falling from said lumbar spine therapy device while said device is in operation and to prevent said patient from slipping on said device when in operation.

10. The lumber spine therapy device of claim 8 which further comprises a mobilization means for enabling said lumbar spine therapy device to be easily transported as desired.

* * * * *